United States Patent
Thakur et al.

(10) Patent No.: US 9,918,649 B2
(45) Date of Patent: Mar. 20, 2018

(54) REPRESENTATION AND IDENTIFICATION OF ACTIVITY PATTERNS DURING ELECTRO-PHYSIOLOGY MAPPING USING VECTOR FIELDS

(71) Applicant: Boston Scientific Scimed Inc., Maple Grove, MN (US)

(72) Inventors: Pramodsingh H. Thakur, White Bear Lake, MN (US); Shibaji Shome, Arden Hills, MN (US); Shantha Arcot-Krishnamurthy, Vadnais Heights, MN (US); Allan C. Shuros, St. Paul, MN (US); Barun Maskara, Blaine, MN (US); Sunipa Saha, Shoreview, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 924 days.

(21) Appl. No.: 14/120,369

(22) Filed: May 14, 2014

(65) Prior Publication Data

US 2014/0343388 A1    Nov. 20, 2014

Related U.S. Application Data

(60) Provisional application No. 61/823,386, filed on May 14, 2013.

(51) Int. Cl.
*A61B 5/04*     (2006.01)
*A61N 1/00*     (2006.01)
(Continued)

(52) U.S. Cl.
CPC .......... *A61B 5/04011* (2013.01); *A61B 5/044* (2013.01); *A61B 5/04012* (2013.01);
(Continued)

(58) Field of Classification Search
CPC ...... A61B 18/1492; A61B 2018/00839; A61B 5/6858; A61B 5/042; A61B 2018/00351;
(Continued)

(56) References Cited

U.S. PATENT DOCUMENTS 4,649,924 A    3/1987   Taccardi
4,674,518 A    6/1987   Salo
(Continued)

FOREIGN PATENT DOCUMENTS

CN    1253761 A     5/2000
CN    101933803 A    1/2011
(Continued)

OTHER PUBLICATIONS

International Search Report and Written Opinion issued in PCT/US2016/053613, dated Jan. 4, 2017, 11 pages.
(Continued)

*Primary Examiner* — Joseph Stoklosa
*Assistant Examiner* — Brian M Antiskay
(74) *Attorney, Agent, or Firm* — Faegre Baker Daniels LLP

(57) ABSTRACT

A method and system for mapping an anatomical structure includes sensing activation signals of intrinsic physiological activity with a plurality of mapping electrodes disposed in or near the anatomical structure, each of the plurality of mapping electrodes having an electrode location. A vector field map which represents a direction of propagation of the activation signals at each electrode location is generated to identify a signature pattern and a location in the vector field map according to at least one vector field template. A target location of the identified signature pattern is identified according to a corresponding electrode location.

6 Claims, 5 Drawing Sheets

(51) Int. Cl.
*A61B 5/042* (2006.01)
*A61B 5/044* (2006.01)
*A61B 5/0402* (2006.01)
*A61B 5/00* (2006.01)
*A61B 5/0452* (2006.01)
*G06K 9/00* (2006.01)
*A61B 18/14* (2006.01)
*A61B 18/00* (2006.01)

(52) U.S. Cl.
CPC ........ *A61B 5/0422* (2013.01); *A61B 5/04023* (2013.01); *A61B 5/04525* (2013.01); *A61B 5/6852* (2013.01); *A61B 5/7221* (2013.01); *A61B 5/7246* (2013.01); *G06K 9/00496* (2013.01); *A61B 5/6858* (2013.01); *A61B 5/6859* (2013.01); *A61B 5/7203* (2013.01); *A61B 18/1492* (2013.01); *A61B 2018/00357* (2013.01); *A61B 2018/00577* (2013.01)

(58) Field of Classification Search
CPC .............. A61B 5/04011; A61B 5/0538; A61B 2018/00214; A61B 2018/00357; A61B 2018/00577; A61B 5/044; A61B 5/0452; A61B 8/0883; A61B 2017/00053; A61B 5/04012; A61B 5/4836; A61B 5/7203; A61B 18/24; A61B 2018/00267; A61B 5/02405; A61B 5/04; A61B 5/0402; A61B 5/04085; A61B 5/04525; A61B 5/046; A61B 5/0464
USPC .................... 607/115–116, 122–123, 131
See application file for complete search history.

(56) References Cited

U.S. PATENT DOCUMENTS

| | | |
|---|---|---|
| 4,840,182 A | 6/1989 | Carlson |
| 4,920,490 A | 4/1990 | Isaacson |
| 5,156,151 A | 10/1992 | Imran |
| 5,284,142 A | 2/1994 | Goble et al. |
| 5,297,549 A | 3/1994 | Beatty et al. |
| 5,300,068 A | 4/1994 | Rosar et al. |
| 5,341,807 A | 8/1994 | Nardella |
| 5,381,333 A | 1/1995 | Isaacson et al. |
| 5,469,858 A | 11/1995 | Osborne |
| 5,480,422 A | 1/1996 | Ben-Haim |
| 5,483,968 A | 1/1996 | Adam et al. |
| 5,500,011 A | 3/1996 | Desai |
| 5,553,611 A | 9/1996 | Budd et al. |
| 5,568,809 A | 10/1996 | Ben-Haim |
| 5,577,502 A | 11/1996 | Darrow et al. |
| 5,588,429 A | 12/1996 | Isaacson et al. |
| 5,634,469 A | 6/1997 | Bruder et al. |
| 5,647,870 A | 7/1997 | Kordis et al. |
| 5,662,108 A | 9/1997 | Budd et al. |
| 5,687,737 A | 11/1997 | Branham et al. |
| 5,697,377 A | 12/1997 | Wittkampf |
| 5,704,365 A | 1/1998 | Albrecht et al. |
| 5,722,402 A | 3/1998 | Swanson et al. |
| 5,810,740 A | 9/1998 | Paisner |
| 5,840,025 A | 11/1998 | Ben-Haim |
| 5,840,031 A | 11/1998 | Crowley |
| 5,846,198 A | 12/1998 | Killmann |
| 5,848,972 A | 12/1998 | Triedman et al. |
| 5,876,336 A | 3/1999 | Swanson et al. |
| 5,921,982 A | 7/1999 | Lesh et al. |
| 5,954,665 A | 9/1999 | Ben-Haim |
| 5,971,933 A | 10/1999 | Gopakumaran et al. |
| 5,983,126 A | 11/1999 | Wittkampf |
| 6,014,581 A | 1/2000 | Whayne et al. |
| 6,050,267 A | 4/2000 | Nardella et al. |
| 6,070,094 A | 5/2000 | Swanson et al. |
| 6,095,150 A | 8/2000 | Panescu et al. |
| 6,167,296 A | 12/2000 | Shahidi |
| 6,226,542 B1 | 5/2001 | Reisfeld |
| 6,233,491 B1 | 5/2001 | Kordis et al. |
| 6,236,886 B1 | 5/2001 | Cherepenin et al. |
| 6,240,307 B1 | 5/2001 | Beatty et al. |
| 6,246,898 B1 | 6/2001 | Vesely et al. |
| 6,254,536 B1 | 7/2001 | DeVito |
| 6,278,894 B1 | 8/2001 | Salo et al. |
| 6,298,257 B1 | 10/2001 | Hall et al. |
| 6,301,496 B1* | 10/2001 | Reisfeld ............ A61B 5/04011 345/419 |
| 6,308,093 B1 | 10/2001 | Armoundas et al. |
| 6,314,310 B1 | 11/2001 | Ben-Haim et al. |
| 6,317,619 B1 | 11/2001 | Boernert et al. |
| 6,318,375 B1 | 11/2001 | Plicchi et al. |
| 6,360,123 B1 | 3/2002 | Kimchi et al. |
| 6,368,285 B1 | 4/2002 | Osadchy et al. |
| 6,400,981 B1 | 6/2002 | Govari |
| 6,490,474 B1 | 12/2002 | Willis et al. |
| 6,516,807 B1 | 2/2003 | Panescu et al. |
| 6,547,082 B1 | 4/2003 | Babini |
| 6,556,695 B1 | 4/2003 | Packer et al. |
| 6,574,492 B1 | 6/2003 | Ben-Haim et al. |
| 6,574,498 B1 | 6/2003 | Gilboa |
| 6,593,884 B1 | 7/2003 | Gilboa et al. |
| 6,600,948 B2 | 7/2003 | Boaz et al. |
| 6,603,996 B1 | 8/2003 | Beatty et al. |
| 6,631,290 B1 | 10/2003 | Guck et al. |
| 6,640,119 B1 | 10/2003 | Budd et al. |
| 6,650,927 B1 | 11/2003 | Keidar |
| 6,690,963 B2 | 2/2004 | Ben-Haim et al. |
| 6,701,176 B1 | 3/2004 | Halperin et al. |
| 6,728,562 B1 | 4/2004 | Budd et al. |
| 6,735,465 B2 | 5/2004 | Panescu |
| 6,773,402 B2 | 8/2004 | Govari et al. |
| 6,807,439 B2 | 10/2004 | Edwards et al. |
| 6,839,588 B1 | 1/2005 | Rudy |
| 6,847,839 B2 | 1/2005 | Ciaccio et al. |
| 6,872,428 B2 | 3/2005 | Yang et al. |
| 6,892,090 B2 | 5/2005 | Verard et al. |
| 6,892,091 B1 | 5/2005 | Ben-Haim et al. |
| 6,893,588 B2 | 5/2005 | Lawson et al. |
| 6,939,309 B1 | 9/2005 | Beatty et al. |
| 6,941,166 B2 | 9/2005 | MacAdam et al. |
| 6,957,101 B2 | 10/2005 | Porath et al. |
| 6,978,168 B2 | 12/2005 | Beatty et al. |
| 6,984,207 B1 | 1/2006 | Sullivan et al. |
| 6,990,370 B1 | 1/2006 | Beatty et al. |
| 7,016,719 B2 | 3/2006 | Rudy et al. |
| 7,043,292 B2 | 5/2006 | Tarjan et al. |
| 7,136,694 B2 | 11/2006 | Hadley et al. |
| 7,263,397 B2 | 8/2007 | Hauck et al. |
| 7,505,810 B2 | 3/2009 | Harlev et al. |
| 7,515,954 B2 | 4/2009 | Harlev et al. |
| 7,628,757 B1 | 12/2009 | Koh |
| 7,629,981 B1 | 12/2009 | West |
| 7,729,752 B2 | 6/2010 | Harlev et al. |
| 8,103,338 B2 | 1/2012 | Harlev et al. |
| 8,137,343 B2 | 3/2012 | Harlev et al. |
| 8,463,368 B2 | 6/2013 | Harlev et al. |
| 8,498,699 B2 | 7/2013 | Wells et al. |
| 8,571,647 B2 | 10/2013 | Harlev et al. |
| 8,744,566 B2 | 6/2014 | Harlev et al. |
| 8,768,440 B1 | 7/2014 | Brodnick et al. |
| 9,113,809 B2 | 8/2015 | Harlev et al. |
| 9,510,769 B2 | 12/2016 | Harlev et al. |
| 9,636,032 B2 | 5/2017 | Thakur et al. |
| 2002/0065459 A1 | 5/2002 | MacAdam et al. |
| 2002/0151807 A1 | 10/2002 | Goldin |
| 2003/0018251 A1 | 1/2003 | Solomon |
| 2003/0065271 A1 | 4/2003 | Khoury |
| 2003/0076277 A1 | 4/2003 | Muramatsu et al. |
| 2003/0078509 A1 | 4/2003 | Panescu |
| 2003/0093067 A1 | 5/2003 | Panescu |
| 2003/0216630 A1 | 11/2003 | Jersey-Willuhn et al. |
| 2004/0059237 A1 | 3/2004 | Narayan et al. |
| 2004/0077942 A1 | 4/2004 | Hall et al. |
| 2004/0097806 A1 | 5/2004 | Hunter et al. |
| 2004/0158165 A1 | 8/2004 | Yonce et al. |

(56) References Cited

U.S. PATENT DOCUMENTS

| | | |
|---|---|---|
| 2004/0243015 A1 | 12/2004 | Smith et al. |
| 2004/0254437 A1 | 12/2004 | Hauck et al. |
| 2005/0037489 A1 | 2/2005 | Gepstein et al. |
| 2005/0038337 A1 | 2/2005 | Edwards |
| 2005/0054918 A1 | 3/2005 | Jasbira |
| 2005/0107834 A1 | 5/2005 | Freeman et al. |
| 2005/0154282 A1 | 7/2005 | Li et al. |
| 2005/0288599 A1 | 12/2005 | MacAdam et al. |
| 2006/0085049 A1 | 4/2006 | Cory et al. |
| 2006/0106375 A1* | 5/2006 | Werneth ............ A61B 18/1492 606/32 |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0112276 A1 | 5/2007 | Simms |
| 2007/0197929 A1 | 8/2007 | Porath et al. |
| 2007/0232949 A1 | 10/2007 | Saksena |
| 2007/0255588 A1 | 11/2007 | Hamilton |
| 2007/0265539 A1 | 11/2007 | Hastings et al. |
| 2007/0270688 A1 | 11/2007 | Gelbart et al. |
| 2007/0270703 A1 | 11/2007 | He et al. |
| 2007/0287902 A1 | 12/2007 | Kristine Fuimaono et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0137934 A1 | 6/2008 | Sakaguchi et al. |
| 2008/0188765 A1 | 8/2008 | Stolarski et al. |
| 2008/0190438 A1 | 8/2008 | Harlev et al. |
| 2008/0221566 A1 | 9/2008 | Krishnan |
| 2008/0222109 A1* | 9/2008 | Sakurai ............ G06K 9/00496 |
| 2008/0234588 A1 | 9/2008 | Feldman et al. |
| 2008/0249424 A1 | 10/2008 | Harlev et al. |
| 2008/0269813 A1 | 10/2008 | Greenhut et al. |
| 2009/0171274 A1 | 7/2009 | Harlev et al. |
| 2009/0177072 A1 | 7/2009 | Harlev et al. |
| 2009/0253976 A1 | 10/2009 | Harlev et al. |
| 2010/0023082 A1 | 1/2010 | Dong et al. |
| 2010/0094274 A1* | 4/2010 | Narayan ............ A61B 5/046 606/33 |
| 2010/0268059 A1 | 10/2010 | Ryu et al. |
| 2010/0286551 A1 | 11/2010 | Harlev et al. |
| 2011/0098771 A1* | 4/2011 | Thakur ............ A61B 5/053 607/27 |
| 2011/0206256 A1 | 8/2011 | Ramanathan et al. |
| 2011/0251505 A1 | 10/2011 | Narayan et al. |
| 2011/0288605 A1 | 11/2011 | Kaib et al. |
| 2012/0029504 A1 | 2/2012 | Afonso et al. |
| 2012/0184858 A1 | 7/2012 | Harlev et al. |
| 2012/0184863 A1 | 7/2012 | Harlev et al. |
| 2012/0184865 A1 | 7/2012 | Harlev et al. |
| 2012/0191087 A1* | 7/2012 | Pachon Mateos . A61B 5/04017 606/34 |
| 2013/0035576 A1 | 2/2013 | O'Grady et al. |
| 2013/0079645 A1 | 3/2013 | Amirana et al. |
| 2013/0274582 A1* | 10/2013 | Afonso ............ A61B 5/0422 600/374 |
| 2013/0310702 A1 | 11/2013 | Reinders et al. |
| 2014/0052118 A1* | 2/2014 | Laske ............ A61B 5/6852 606/32 |
| 2014/0200874 A1 | 7/2014 | Zeng et al. |
| 2014/0235986 A1 | 8/2014 | Harlev et al. |
| 2014/0330150 A1 | 11/2014 | Thakur et al. |
| 2015/0254419 A1 | 9/2015 | Laughner et al. |
| 2015/0254893 A1 | 9/2015 | Laughner et al. |
| 2016/0051204 A1 | 2/2016 | Harlev et al. |

FOREIGN PATENT DOCUMENTS

| | | |
|---|---|---|
| CN | 102917638 A | 2/2013 |
| EP | 2204120 A1 | 7/2010 |
| EP | 2427106 A | 3/2012 |
| EP | 2485194 A2 | 8/2012 |
| WO | 1999005971 A1 | 2/1999 |
| WO | WO2006037172 A1 | 4/2006 |
| WO | 2006066324 A1 | 6/2006 |
| WO | 2007035306 A2 | 3/2007 |
| WO | 2007035306 A3 | 3/2007 |
| WO | 2007108776 A2 | 9/2007 |
| WO | 2007146864 A3 | 12/2007 |
| WO | 2008138009 A1 | 11/2008 |
| WO | 2010054320 A1 | 5/2010 |
| WO | 2010129095 A2 | 11/2010 |
| WO | WO2012037471 A2 | 3/2012 |
| WO | 2012092016 A1 | 7/2012 |
| WO | 2013006713 A2 | 1/2013 |
| WO | 2014185977 A1 | 11/2014 |
| WO | 2015134248 A1 | 9/2015 |

OTHER PUBLICATIONS

He, Ye H., "An interactive graphical system for automated mapping and display of cardiac rhythms", Journal of Electrocardiology, vol. 32, No. 3, Jul. 1, 1999, pp. 225-241.
International Preliminary Report on Patentability issued in PCT/US2014/000114, dated Nov. 26, 2015, of 9 pages.
International Preliminary Report on Patentability issued in PCT/US2014/036939, dated Nov. 19, 2015, 8 pages.
International Search Report and Written Opinion issued in PCT/US2014/036939, dated Jul. 30, 2014, 11 pages.
International Search Report and Written Opinion issued in PCT/US2015/017289, dated May 6, 2015, 10 pages.
International Search Report and Written Opinion issued in PCT/US2015/017482, dated Jun. 5, 2015, 9 pages.
Buneo, Christopher A., Analyzing Neural Responses with Vector Fields, Journal of Neuroscience Methods, vol. 197, 2011, pp. 109-117.
He, Ye H. et al., "An interactive Graphical System for Automated Mapping and Display of Cardiac Rhythms", Journal of Electrocardiology, vol. 32, No. 3, 1999, 17 pages.
Holm, Magnus et al., "A New Method for Analysis of Atrial Activation During Chronic Atrial Fibrillation in Man", IEEE Transactions on Biomedical Engineering, vol. 43, No. 2, Feb. 1996, 14 pages.
International Search Report and Written Opinion issued in PCT/US2014/000114, dated Sep. 8, 2014, 12 pages.
Adams et al., "Seeded Region Growing", IEEE Transactions on Pattern Analysis and Machine Intelligence, 16 (6):641-647, 1994.
Arthur et al., "Clinical Use of Intracardiac Impedance: Current Applications and Future Perspectives", PACE, vol. 24, No. 4, Part 1, Apr. 2001, pp. 500-506.
Baan, Jan et al., "Continuous Measurement of Left Ventricular Volume In Animals and Humans by Conductance Catheter", Diagnostic Methods-Conductance Catheter, Circulation, vol. 70, No. 5, 1984, pp. 812-823.
Badics et al., "Real-Time Reconstruction of Endocardial Potential Maps in Non-Contact Cardiac Mapping", International Journal for computation and Mathematics in Electrical and Electronic Engineering (COMPEL), vol. 28, No. 4, 2009.
Ben-Haim et al., "Nonfluoroscopic, in Vivo Navigation and Mapping Technology", Nature Medicine, 2(12):1393-1395, Dec. 1996.
Besl et al., "A Method for Registration of 3-D Shapes", IEEE Transactions on Pattern Analysis and Machine Intelligence, 14(2):239-256, Feb. 1992.
Blomstrom-Lundqvist et al., "ACC/AHA/ESC Guidelines for the Management of Patients With Supraventricular Arrhythmias-Executive Summary", Journal of the American College of Cardiology, 42(8):1493-1531, 2003.
Breithardt et al., "AHA Medical/Scientific Statement—Special Report: Standards for Analysis of Ventricular Late Potentials Using High-Resolution or Signal-Averaged Electrocardiography", Circulation, 83(4):1481-1488, Apr. 1991.

(56) References Cited

OTHER PUBLICATIONS

Brooks et al., "Electrical Imaging of the Heart", IEEE Signal Processing Magazine, pp. 24-42, 1997.
Caspi et al., "Stem Cell Research: Regenerating the Heart Using Human Embryonic Stem Cells—from Cell to Bedside", IMAJ 8:208-214, 2006.
Cheney et al., "Electrical Impedance Tomography", SIAM Review 41(1):85-101, 1999.
Communication pursuant to Article 94(3) EPC issued in EP Application No. 07 798 369.0, dated Nov. 17, 2011, 5 pages.
De Groot et al., "Three-Dimensional Catheter Positioning During Radiofrequency Ablation in Patients: First Application of a Real-Time Position Management System", Journal of Cardiovascular Electrophysiology, 11(11):1183-1192, Nov. 2000.
Donahue et al., "Focal Modification of Electrical Conduction in the Heart by Viral Gene Transfer", Nature Medicine, 6 (12):1395-1398, 2000.
Dong et al., "Integrated Electroanatomic Mapping With Three-Dimensional Computed Tomographic Images for Real-Time Guided Ablations", Circulation 113:186-194, 2006.
Durrer et al., "Total Excitation of the Isolated Human Heart", Circulation, vol. XLI, pp. 899-912, 1970.
E. J. Haug et al.: Design Sensitivity Analysis of Structural Systems, Mathematics in Science and Engineering, vol. 177 (1986).
Ector et al., "Cardiac Three-Dimensional Magnetic Resonance Imaging and Fluoroscopy Merging—A New Approach for Electroanatomic Mapping to Assist Catheter Ablation", Circulation, (Dec. 13, 2005), pp. 3769-3776.
Extended European Search Report issued in EP Application No. 10 772 414, dated May 7, 2013, 6 pages.
Fletcher, R. "Chapter 6: Sums of Squares and Nonlinear Equations," Practical Methods of Optimization, 2nd Edition, J. Whey & Sons, pp. 110-119 (1987).
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart 2002, 87:575-582.
Geddes. L.A.et al., "Criteria for the Selection of Materials for Implanted Electrodes", Annals of Biomedical Engineering, vol. 31, pp. 879-890 (2003).
Gepstein et al., "A Novel Method for Nonfluoroscopic Catheter-Based Electroanatomical Mapping of the Heart", Circulation 95:1611-1622, 1997.
Gitosusastro et al., Performance Derivative Calculations and Optimization Process, IEEE Transactions on Magnetics. vol. 25, No. 4 (Jul. 1989) pp. 2834-2839.
Hansen: Rank-Deficient and Discrete Ill-Posed Problems: Numerical Aspects of Linear Inversion, SIAM, Philadelphia. USA, pp. 100-119, 1998.
Huang, Yi-Chih ct al., "Development of a Third Generation Intraventricular Impedance Imaging (III) System: Evaluation of Hardware Design", Engineering in Medicine and Biology Society,. Proceedings of the 19th Annual International Conference of the IEEE, Oct. 30-Nov. 2, 1997 vol. 6, pp. 336-338 (1997).
International Preliminary Report on Patentability in PCT/US2007/070854, dated Dec. 16, 2008, 9 pages.
International Preliminary Report on Patentability in PCT/US2009/061277, dated May 3, 2011 11 pages.
International Preliminary Report on Patentability in PCT/US2010/027568 dated Oct. 25, 2011, 4 pages.
International Preliminary Report on Patentability issued in PCT/US2008/05235 dated Aug. 11, 2009, 6 pages.
International Preliminary Report on Patentability issued in PCT/US2009/036099, dated Oct. 14, 2010, 20 pages.
International Preliminary Report on Patentability issued in PCT/US2010/027436, dated Nov. 9, 2011, 4 pages.
International Search Report and the Written Opinion in PCT/US08/52385 dated Aug. 3, 2003, 11 pages.
International Search Report and Written Opinion in PCT/US2010/027563, dated Nov. 4, 2010, 6 pages.
International Search Report and Written Opinion in PCT/US2012/020946, dated May 7, 2012, 15 pages.
International Search Report and Written Opinion issued in PCT/US2007/070854, dated Sep. 12, 2008, 10 pages.
International Search Report and Written Opinion issued in PCT/US2009/036099, dated Apr. 28, 2009, 21 pages.
International Search Report and Written Opinion issued in PCT/US2009/061277, dated Apr. 8, 2010, 12 pages.
Jain et al., "Cell Therapy Attenuates Deleterious Ventricular Remodeling and Improves Cardiac Performance after Myocardial Infarction", Circulation, 103:1920-1927, 2001.
Jalife, "Rotors and Spiral Waves in Atrial Fibrillation", Journal of Cardiovascular Electrophysiology, 14:776-730, 2003.
Jane et al., "Alignment Methods for Averaging of High-Resolution Cardiac Signals: A Comparative Study of Performance", IEEE Transactions on Biomedical Engineering, 38(6):571-579, 1991.
Japanese Office Action in JP Application No. 2009-515586, dated Jun. 26, 2012, 4 pages (0002JP1).
Jia et al., "Electrophysiologic Endocardial Mapping from a Noncontact Nonexpandable Catheter: A Validation Study a Geometry-Based Concept". Journal of Cardiovascular Electrophysiology, 11:1238-1251, 2000.
Kikuchi et al., "Targeted Modification of Atrial Electrophysiology by Homogeneous Transmural Atrial Gene Transfer", Circulation, 111:264-270, 2005.
Kistler et al., "Validation of Three-Dimensional Cardiac image Integration; Use of Integrated CT image into Electroanatomic Mapping System to Performa Catheter Ablation of Atrial Fibrillation", Journal of Cardiovascular Electrophysiology, 17:341-348, 2006.
Kuklik et al., "The reconstruction, from a set of points, and analysis of the interior surface of the heart chamber", Physiol. Meas. 25:617-627, 2004.
Kun, Stevan et al., "Conductance Volumetric Model of an Eccentrically Positioned Catheter Within a Three-Compartment Ellipsoidal Ventricle", IEEE Transactions on Biomedical Engineering, vol. 40, No. 6, Jun. 1993, pp. 589-592.
L. Piegl, W, Tiller: The NURBS Book, 2nd Edition, Monographs in Visual Communication, Springer (1997).
Lacair et al., Improved Alignment Method for Noisy High-Resolution ECG and Holter Records Using a Multiscale Cross-Correlation, IEEE Transactions on Biomedical Engineering, 50(3), pp. 344-353, 2003.
International Preliminary Report on Patentability issued in PCT/US2015/0017289 dated Sep. 15, 2016, 8 pages.
International Preliminary Report on Patentability issued in PCT/US2015/017482 dated Sep. 15, 2016, 4 pages.
International Search Report and Written Opinion issued in PCT/US2010/027436 dated Oct. 27, 2010, 10 pages.
Supplemental European Search Report issued in EP App[lication 10772414.8, dated May 7, 2013, 6 pages.
Andras Lasso et al., "SlicerWiki VolumeClip", Dec. 25, 2014, pp. 1-4, XP55332376, retrieved from teh internet: https://www.slicer.org/wiki/Documentation/4.4/Extensions/VolumeClip, retrieved on Jan. 5, 2017.
Anonymous: Solid Commands—Rhino 3-D Modeling (Rhinoceros 5), Sep. 17, 2015, XP055332631, Retrieved from Internet: http://docs.mcneel.com/rhino/5/help/en-us/seealso/sak_solidtools.htm, retrieved on Jan. 5, 2017, see under Cap, 2 pages.
International Search Report and Written Opinion issued in PCT/US2016/053630, dated Jan. 17, 2017, 12 pages.
International Search Report and Written Opinion issued in PCT/US2016/053633, dated Jan. 17, 2017, 14 pages.
Liu et al., "Endocardial Potential Mapping from a Noncontact Nonexpandable Catheter: A Feasibility Study", Annals of Biomedical Engineering, 26:994-1009, 1998.
Lorensen et al. "Marching Cubes: A High Resolution 3D Surface Construction Algorithm", Computer Graphics, 21 (4):103-109, Jul. 1987.
Makela et al., "A Review of Cardiac Image Registration Methods", IEEE Transactions on Medical Imaging, 21 (9):1011-1021, Sep. 2002.

(56) References Cited

OTHER PUBLICATIONS

Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252.

Mangan, Alan et al., "Partitioning 3D Surface Meshes Using Watershed Segmentation", IEEE Transactions on Visualization and Computer Graphics, vol. 05, No. 4, pp. 308-321, (Oct.-Dec. 1999).

Meininger et al., "Initial Experience with a Novel Focused Ultrasound Ablation System for Ring Ablation Outside the Pulmonary Vein", Journal of Interventional Cardiac Electrophysiology, 8:141-148, 2003.

Merrill, Daniel R. et al., "Electrical stimulation of excitable tissue: design of efficacious and safe protocols", Journal of Neuroscience Methods, vol. 141, pp. 171-198 (2005).

Miller, "Editors Forum—Application of Registration for Ablation: A Marriage of Technologies", Journal of Interventional Cardiac Electrophysiology, 11:87-89, 2004.

Nademanee et al., "A New Approach for Catheter Ablation of Atrial Fibrillation: Mapping of the Electrophysiologic Substrate", Journal of the American College of Cardiology, 43(11):2044-2053, 2004.

Non-final Office Action issued in U.S. Appl. No. 11/451,898, dated Sep. 25, 2008, 13 pages.

Non-final Office Action issued in U.S. Appl. No. 11/451,908, dated Sep. 4, 2008, 12 pages.

Noseworthy et al., "The Impact of Respiration on Left Atrial and Pulmonary Venous Anatomy: Implications for Image-Guided Intervention", Heart Rhythm, 2(11), pp. 1173-1178, Nov. 2005.

Pappone et al., "Robotic Magnetic Navigation for Atrial Fibrillation Ablation", Journal of the American College of Cardiology; 47(7):1390-1400, 2006.

Paragios, "A Level Set Approach for Shape-Driven Segmentation and Tracking of the Left Ventricle", IEEE Transactions on Medical Imaging, 22(6):773-776, Jun. 2003.

Persson et al., "A Simple Mesh Generator in MATLAB", SIAM Review, 46(2):329-345, 2004.

Persson, "Mesh Generation for Implicit Geometries", Massachusetts Institute of Technology—Thesis, Feb. 5, 2006.

Pham, Dzung et al., "Current Methods in Medical Image Segmentation", Annu. Rev. Biomed. Eng., 02: pp. 315-337, (2000).

Rao et al., "Novel Noncontact Catheter System for Endocardial Electrical and Anatomical Imaging", Annals of Biomedical Engineering, 32(4):573-584, 2004.

Reddy et al., "Integration of Cardiac Magnetic Resonance Imaging With Three-Dimensional Electroanatomic Mapping to Guide Left Ventricular Catheter Manipulation—Feasibility in a Porcine Model of Healed Myocardial Infarction", Journal of the American College of Cardiology, 44(11):2202-2213, 2004.

Reddy et al., "Use of a Diode Laser Balloon Ablation Catheter to Generate Circumferential Pulmonary Venous . Lesions in an Open-Thoracotomy Caprine Model", PACE, 27:52-57, 2004.

Sanders et al., "Spectral Analysis Identifies Sites of High-Frequency Activity Maintaining Atrial Fibrillation in Humans", Circulation, 112:789-797, 2005.

Sethian, "Level Set Methods and Fast Marching Methods: Evolving Interfaces in Computational Geometry, Fluid Mechanics, Computer Vision, and Materials Science", Department of Mathematics-University of California, Berkeley, Cambridge University Press, 1999.

Simon et al., "Electroanatomic Mapping of the Right Atrium With a Right Atrial Basket Catheter and Three-Dimensional Intracardiac Echocardiography", PACE, 27:318-326, 2004.

Smits et al., "Catheter-Based Intramyocarial Injection of Autologous Skeletal Myoblasts as a Primary Treatment of Ischemic Heart Failure", Journal of the American College of Cardiology, 42(12):2063-2069, 2003.

Solomon et al., "Real-Time Cardiac Catheter Navigation on Three-Dimensional CT Images", Journal of Interventional Cardiac Electrophysiology, 8:27-36, 2003.

Sra et al., "Registration of Three-Dimensional Left Atrial Computed Tomographic Images With Projection Images Obtained Using Fluoroscopy", Circulation, 112:3763-3768, 2005.

Sra, Jasbir et al, "Registration of 3D Computed Tomographic Images With Interventional Systems: Implications for Catheter Ablation of Atrial Fibrillation", J Interv Card Electrophysiol, 16:141-148, 2006.

Stevenson, "Radiofrequency Catheter Ablation of Ventricular Tachycardia After Myocardial Infarction", Circulation, 98:308-314, 1998.

Supplemental European Search Report issued in EP Application No. 09824015, dated Jun. 1, 2012, 7 pages.

Supplementary European Search Report issued in EP Applicaion No. 09727423, dated May 15, 2012, 5 pages.

Supplementary European Search Report issued in EP Application No, 07793369.0 dated Jul. 30 2010, 6 pages.

Supplementary Europeant Search Report issued in EP Application No. 08728501, dated Feb. 25, 2011, 4 pages.

Taccardi et al., "A New Intracavitary Probe for Detecting the Site of the Origin of Ectopic Ventricular Beats During One Cardiac Cycle", Circulation, 75(1):272-281, 1987.

Thal et al., "Novel Applications in Catheter Ablation", Journal of Interventional Cardiac Electrophysiology, 13:17-21, 2005.

Thiagalingam et al., "Noncontact Mapping of the Left Ventricle: Insights from Validation With Transmural Contact Mapping", PACE, 27:570-578, 2004.

Voth, "The Inverse Problem of Electrocardiography: Industrial Solutions and Simulations", BEM and NFSI Conference Proceedings, Minneapolis, MN, May 12-15, 2005, pp. 191-194.

Wittkampf et al., "LocaLisa: New Technique for Real-Time 3-Dimensional Localization of Regular Intracardiac Electrodes", Circulation, 99:1312-1317, 1999.

Yezzi, Anthony et al., "A Geometric Snake Model for Segmentation of Medical Imagery", IEEE Transactions on Medical Imag, vol. 16, No. 2, Apr. 1997.

* cited by examiner

REPRESENTATION AND IDENTIFICATION OF ACTIVITY PATTERNS DURING ELECTRO-PHYSIOLOGY MAPPING USING VECTOR FIELDS

CROSS-REFERENCE TO RELATED APPLICATION

This application claims priority to Provisional Application No. 61/823,386, filed May 14, 2013, which is herein incorporated by reference in its entirety.

TECHNICAL FIELD

The present disclosure relates to cardiac mapping systems. More specifically, the present disclosure relates to a cardiac mapping system configured to display persistent data visualization during an electrophysiological study.

BACKGROUND

Diagnosing and treating heart rhythm disorders often involves the introduction of a catheter having a plurality of sensors/probes into a cardiac chamber through the surrounding vasculature. The sensors detect electric activity of the heart at sensor locations in the heart. The electric activity is generally processed into electrogram signals that represent signal propagation through cardiac tissue at the sensor locations.

Systems can be configured to display the electrical signals detected in the cardiac chamber as an activation map based on voltages detected. These activation maps may require interpolation of the detected voltages to get a finer scale of visualization across multiple electrodes of, for example, a basket catheter adapted for electrophysiological sensing. Furthermore, the decreased range of voltage signals can make automated pattern matching and classification challenging. Robust and reliable visualization of activation signals is paramount to identify accurate therapy targets during mapping. Therefore, it may be beneficial to provide a vector field pattern matching to identify aberrant electrical signals.

SUMMARY

In Example 1, a method for mapping an anatomical structure, the method includes sensing activation signals of intrinsic physiological activity with a plurality of mapping electrodes disposed in or near the anatomical structure, each of the plurality of mapping electrodes having an electrode location, generating a vector field map which represents a direction of propagation of the activation signals at each electrode location, identifying a signature pattern and a location in the vector field map according to at least one vector field template.

In Example 2, the method according to Example 1, wherein generating the vector field map further includes determining a vector of propagation at each electrode which represents a direction of propagation of the sensed activation signal with respect to at least one adjacent electrode.

In Example 3, the method according to either of Example 1 and 2, wherein generating the vector field map further includes determining a reliability index for each sensed activation signal at an electrode location according to at least one of a contact between the corresponding electrode and the anatomical structure and a level of noise in the sensed activation signals, and scaling each vector of the vector field map according to the corresponding reliability index.

In Example 4, the method according to any one of Examples 1-3, wherein identifying the signature pattern further includes receiving a template bank which includes a plurality of vector field templates, each vector field template having a unique signature pattern, comparing the vector field map with each vector field template of the template bank, and identifying the signature pattern that most closely matches the generated vector field map according to a similarity index.

In Example 5, the method according to any one of Examples 1-4, wherein each unique signature pattern of the template bank includes at least one of a divergent pattern representing focal activity having a foci location and a curled pattern representing rotor activity having a core location.

In Example 6, the method according to any one of Examples 1-5, wherein comparing the vector field further includes determining a reliability index for each sensed activation signal at an electrode location according to at least one of a contact between the corresponding electrode and the anatomical structure and a level noise in the sensed activation signal, selecting one or more vectors of the vector field map which meet a preselected threshold based on the determined reliability index, and comparing only the one or more selected vectors with the corresponding vectors within each vector field template of the template bank.

In Example 7, the method according to Example 1, further includes displaying at least one of the generated vector field map and the identified target location.

In Example 8, a method for mapping cardiac tissue includes sensing activation signals of cardiac activity with a plurality of mapping electrodes disposed in or near the anatomical structure, each of the plurality of mapping electrodes having an electrode location, generating a vector field map which represents a direction of propagation of the activation signals at each electrode location and identifying a signature pattern and a location in the vector field map according to at least one vector field template.

In Example 9, the method according to Example 8, wherein generating the vector field map further includes determining a vector at each electrode which represents a direction of propagation of the sensed activation signal with respect to at least one adjacent electrode.

In Example 10, the method according to either of Examples 8-9, wherein generating the vector field map further includes determining a reliability index for each sensed activation signal at an electrode location based on at least one of a contact between the corresponding electrode and adjacent cardiac tissue and a level of noise in the sensed activation signal, and scaling each vector of the vector field map according to the corresponding reliability index.

In Example 11, the method according to any one of Examples 8-10, wherein identifying the signature pattern further includes receiving a template bank which includes a plurality of vector field templates, each vector field template having a unique signature pattern comparing the vector field map with each vector field template of the template bank, and identifying the signature pattern that most closely matches the generated vector field map according to a similarity index.

In Example 12, the method according to any one of Examples 8-11, wherein each unique signature pattern of the template bank includes at least one of a divergent pattern representing focal activity having a foci location and a curled pattern representing rotor activity having a core location.

In Example 13, the method according to any one of Examples 8-12, wherein comparing the vector field further includes determining a reliability index for each sensed activation signal at an electrode location according to a contact between the corresponding electrode and the anatomical structure selecting one or more vectors of the vector field map which meet a preselected threshold based on the determine reliability index, and compare only the one or more selected vectors with the corresponding vectors within each vector field template of the template bank.

In Example 14, a catheter system includes a plurality of mapping electrodes configured to detect activation signals of intrinsic cardiac activity, each of the plurality of mapping electrodes having an electrode location, and a mapping processor associated with the plurality of mapping electrodes, the mapping processor configured to record the detected activation signals and associate one of the plurality of mapping electrodes with each recorded activation signal, the mapping processor further configured to generate a vector field map which represents a direction of propagation of the activation signals at each electrode location, and identify a signature pattern and a location in the vector field map according to at least one vector field template.

In Example 15, the catheter system according to Example 14, wherein to generate the vector field map the processing system is further configured to determine a vector of propagation at each electrode which represents a direction of propagation of the sensed activation signal with respect to at least one adjacent electrode.

In Example 16, the catheter system according to either of Examples 14 and 15, wherein to generate the vector field map the processing system is further configured to determine a reliability index for each sensed activation signal at an electrode location according to at least one of a contact between the corresponding electrode and the anatomical structure and a level of noise in the sensed activation signal, and scale each vector of the vector field map according to the corresponding reliability index.

In Example 17, the catheter system according to any of Examples 14-16, wherein to identify the signature pattern the processing system is further configured to access a template bank which includes a plurality of vector field templates, each vector field template having a unique signature pattern, compare the vector field map with each vector field template of the template bank, and identify the signature pattern most closely matching the generated vector field map according to a similarity index.

In Example 18, the catheter system according to any one of Examples 14-17, wherein each unique signature pattern of the template bank includes at least one of a divergent pattern representing focal activity having a foci location and a curled pattern representing rotor activity having a core location.

In Example 19, the catheter system according to any one of Examples 14-18, wherein to compare the vector field the processing system is further configured to determine a reliability index for each sensed activation signal at an electrode location according to at least one of a contact between the corresponding electrode and the anatomical structure and a level of noise in the sensed activation signal, select one or more vectors of the vector field map which meet a preselected threshold based on the determine reliability index, and compare only the one or more selected vectors with the corresponding vectors within each vector field template of the template bank.

In Example 20, the catheter system according to Example 14, further includes a display device for displaying at least one of the generated vector field map and the identified target location.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
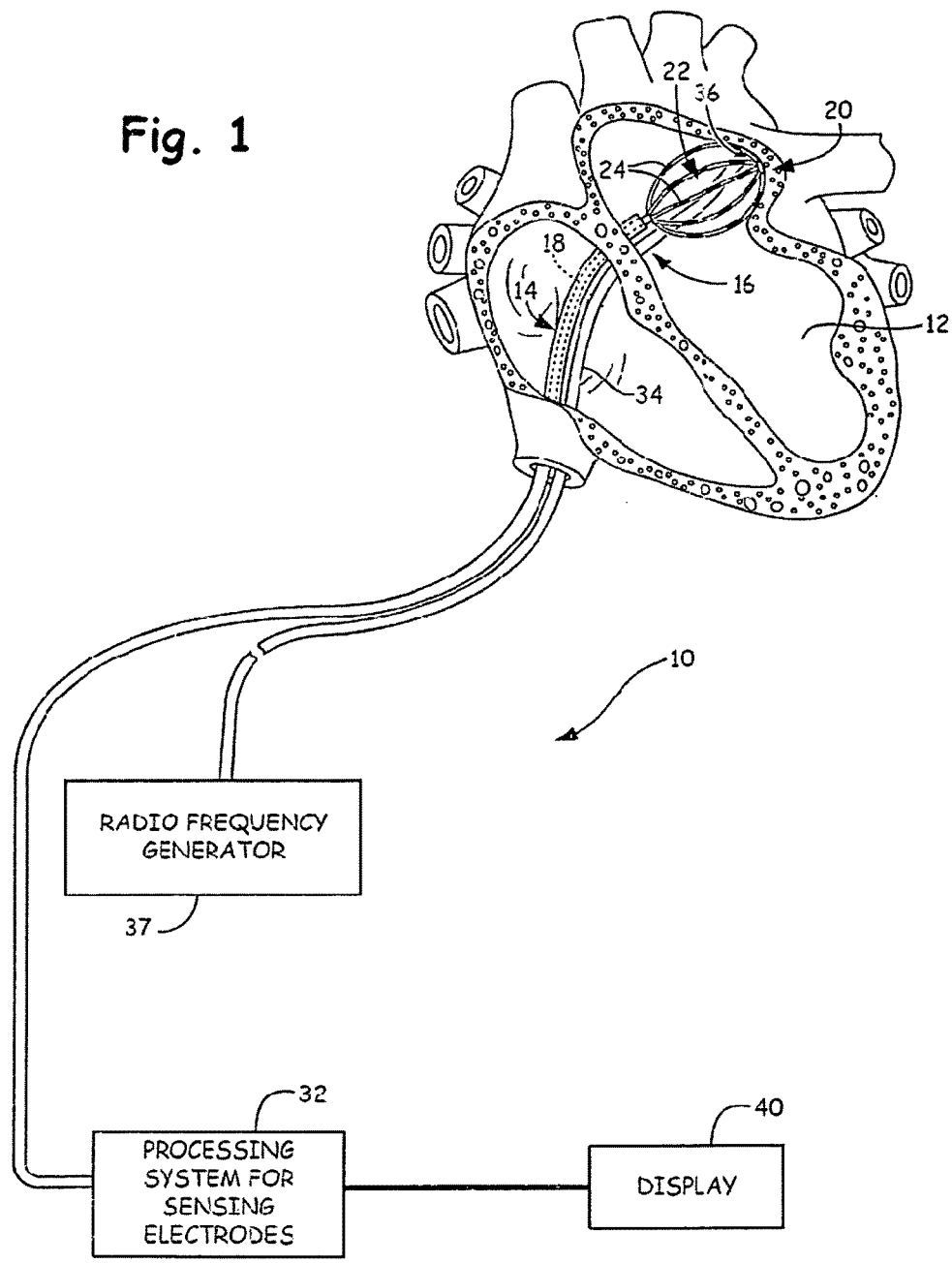
FIG. 1 is a schematic view of an embodiment of a system for accessing a targeted tissue region in the body for diagnostic and therapeutic purposes.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a system 10 for accessing a targeted tissue region in the body for diagnostic or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of mapping electrodes 24 each having an electrode location and channel. Each electrode 24 is configured to sense intrinsic physiological activity in the anatomical region on which the ablation procedure is to be performed. In some embodiments, the electrodes 24 are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g., a vector field map, to identify the site or sites within the heart appropriate for ablation. The processing system 32 identifies a near-field signal component, i.e. activation signals associated with local activation and originating from the tissue adjacent to the mapping electrode 24, from an obstructive far-field signal component, i.e. activation signals originating from non-adjacent tissue, within the sensed activation signals. For example, in an atrial study, the near-field signal component includes activation signals originating from atrial myocardial tissue whereas the far-field signal component includes activation signals originating from the ventricular myocardial tissue. The near-field activation signal component can be further analyzed to find the presence of a pathology and to determine a location suitable for ablation for treatment of the pathology, e.g., ablation therapy.

The processing system 32 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the processing system 32 can take any suitable form.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor or divergent activation pattern in the anatomical feature being mapped. Studies have shown that dominant rotors and/or divergent activation patterns have a role in the initiation and maintenance of atrial fibrillation, and ablation of the rotor path, rotor core, and/or divergent foci may be effective in terminating the atrial fibrillation. In either situation, the processing system 32 processes the sensed activation signals to generate a display of relevant characteristics, such as an voltage map, a vector field map, a contour map, a reliability map, an electrogram, and the like. The relevant characteristics may be used by the physician to identify a site suitable for ablation therapy.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

The processing system 32 outputs to a device 40 the display of relevant characteristics for viewing by a physician. In the illustrated embodiment, device 40 is a CRT, LED, or other type of display, or a printer). The device 40 presents the relevant characteristics in a format most useful to the physician. In addition, the processing system 32 may generate position-identifying output for display on the device 40 that aids the physician in guiding the ablation electrode(s) 36 into contact with tissue at the site identified for ablation.

Figure 2:
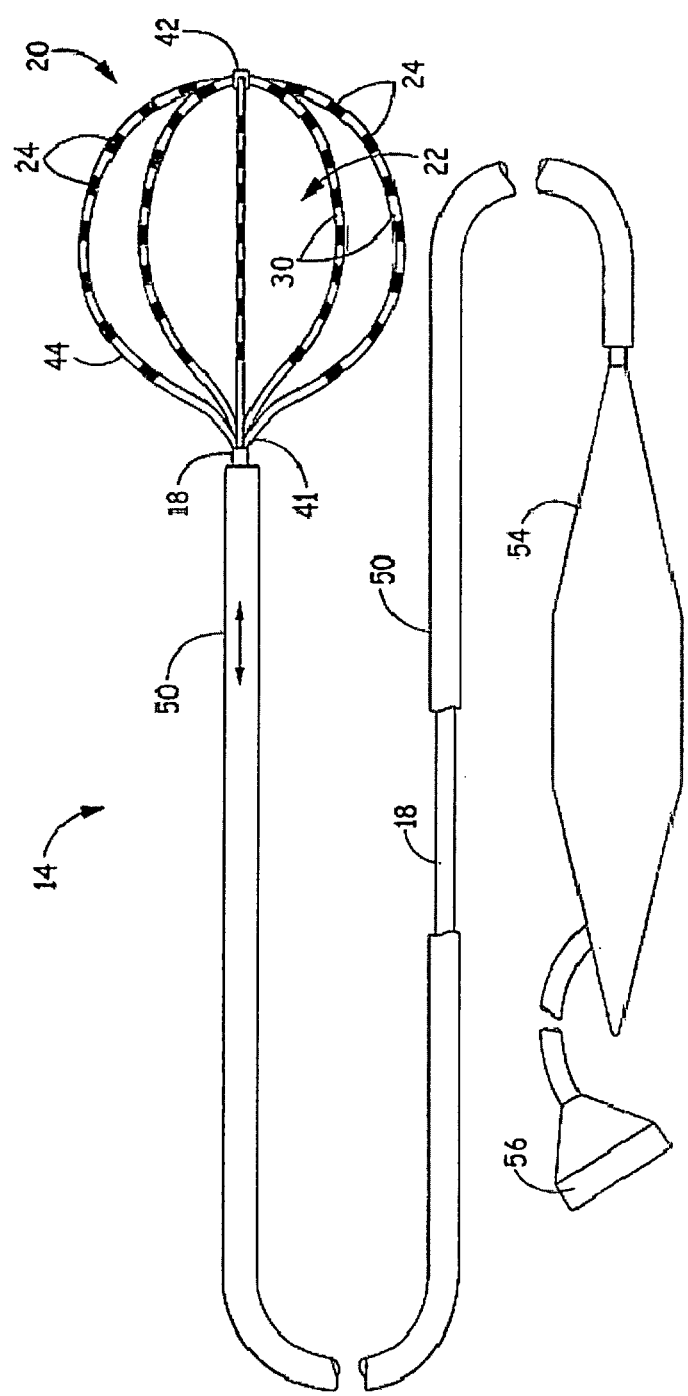
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g., activation signals, in the myocardial tissue, the sensed activity is then processed by the processing system 32 to assist the physician in identifying the site or sites having a heart rhythm disorder or other myocardial pathology via a generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 is movable along the major axis of the catheter body 18. Moving the sheath 50 forward (i.e., toward the distal end) causes the sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby expressly incorporated herein by reference in its entirety.

A signal wire (not shown) is electrically coupled to each mapping electrode 24. The wires extend through the body 18 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signals generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are hereby expressly incorporated herein by reference.

It is noted that other multi-electrode structures could be deployed on the distal end of the mapping catheter 14. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system (not shown). As another example, the ablation electrode at the distal end of the ablation catheter may be coupled to the signal processing system 32 to also operate as a mapping electrode.

Figure 3:
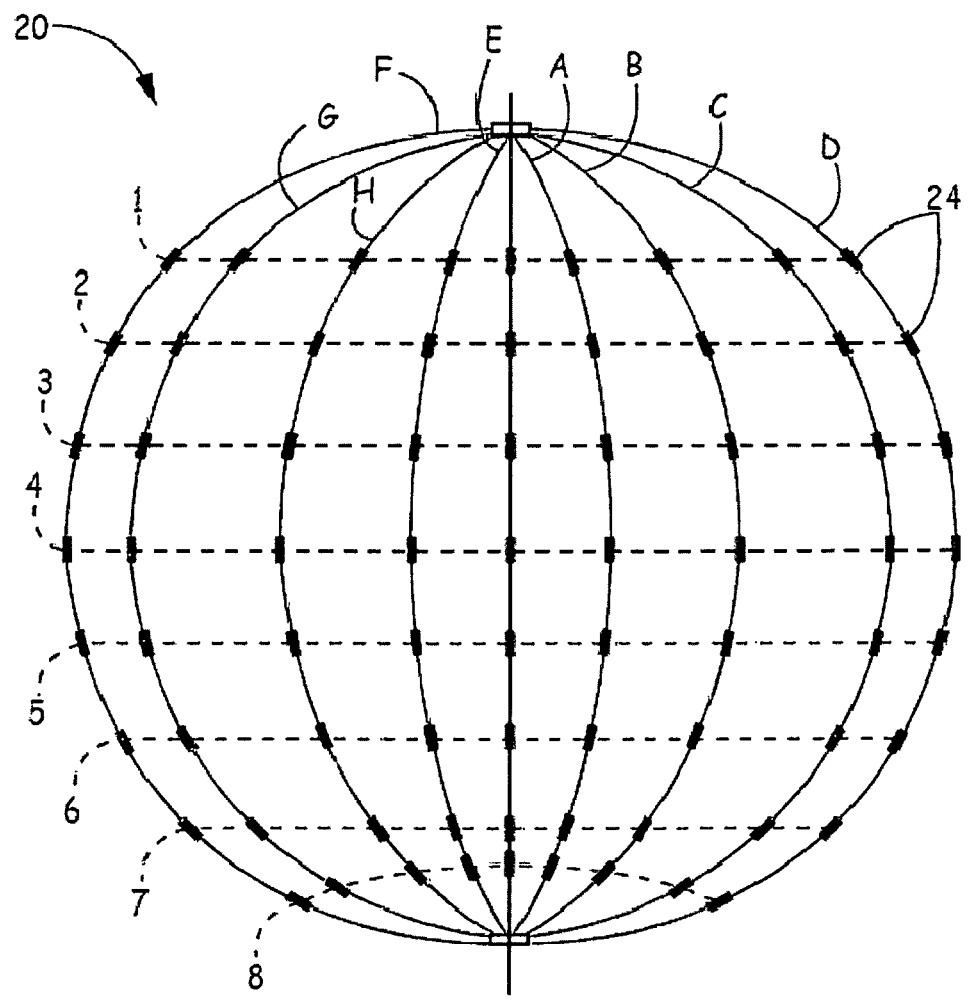
FIG. 3 is a schematic side view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g., left atrium or left ventricle of the heart), the processing system 32 is configured to record the activation signals from each electrode 24 channel related to intrinsic physiological activity of the anatomical structure, i.e. the electrodes 24 measure electrical activation signals intrinsic to the physiology of the anatomical structure.

Figure 4:
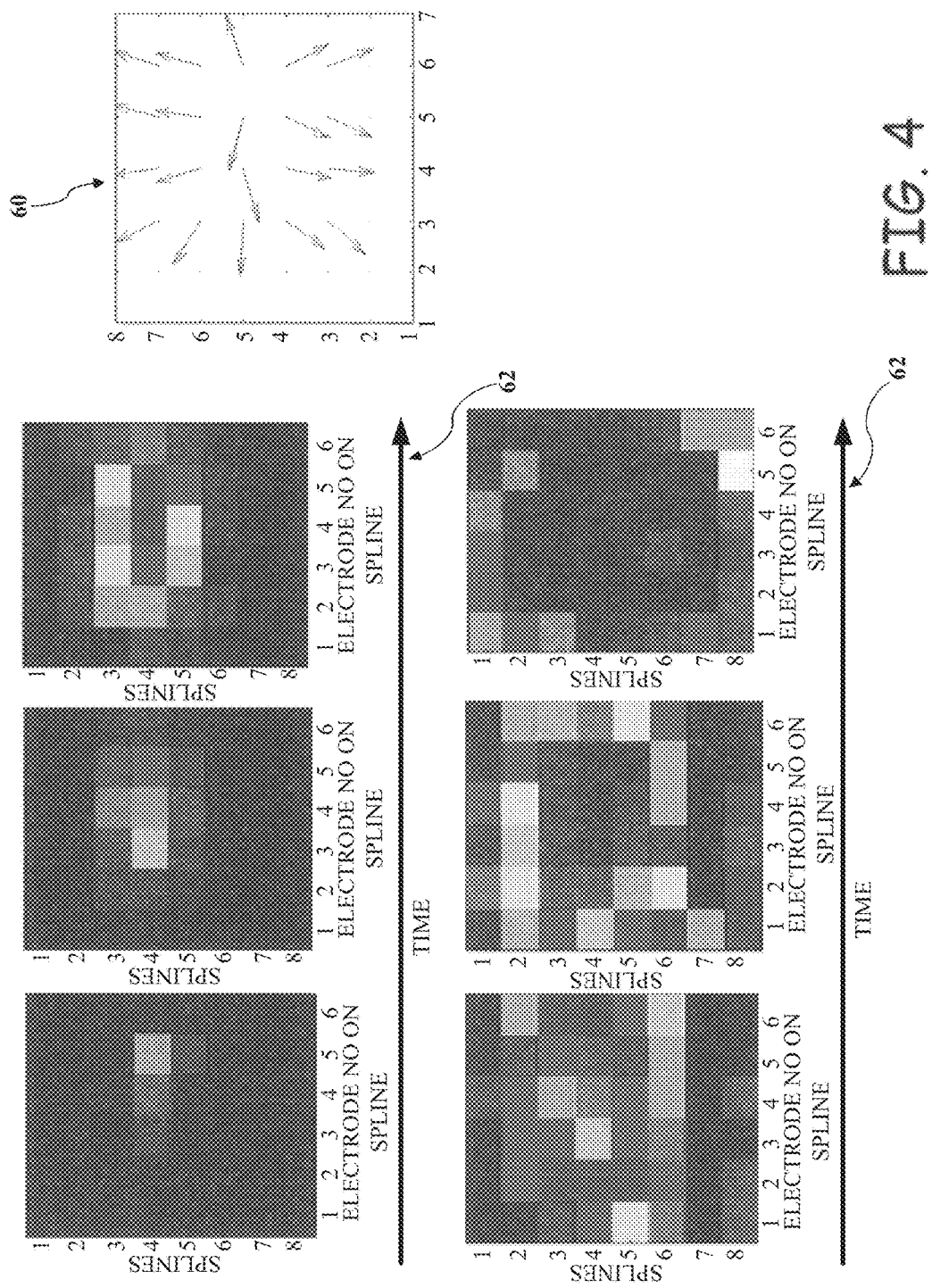
FIG. 4 illustrates a series of consecutive activation maps and a corresponding vector field map generated therefrom.

In some embodiments, the processing system 32 is configured to identify signature patterns in generated vector field maps to locate a rotor activation pattern core or divergent activation pattern foci. With the core and/or foci location, a physician can direct a therapy device, e.g. an ablation catheter, to the identified core and/or foci location to administer the therapy at the corresponding tissue location. The vector field map 60, as illustrated in FIG. 4 (bottom), is a vector field wherein each vector represents a local direction of propagation of the activation signals sensed at each electrode 24 with respect to an adjacent or neighboring electrode 24 during a time period. FIG. 4 (top) illustrates an activation map 62 of an activation signal during atrial fibrillation propagating divergently from a focal point or foci. The processing system 32 senses the activation signals at an electrode location and determines an onset time associated with the activation signal at the current electrode location. To determine the vector corresponding to the propagating activation signal, the processing system 32 calculates a circular average of detected activation signals at adjacent or neighboring electrodes 24 according to latency between an activation signal sensed at a current electrode location and an activation signal sensed at a neighboring electrode location. In some embodiments, the processing system 32 determines each vector according to:

$$V = \arg(\Sigma_\theta (T_\theta - T_0) e^{-i\theta}) \quad \text{equation 1}$$

where $T_0$ is the onset time of an activation signal at a current electrode location, $T_\theta$ is the onset time of the activation signal at a neighboring electrode location located at angle $\theta$. The angle $\theta$ is based on the angle of the adjacent neighboring electrodes 24. For example, eight neighboring electrodes 24 can be used to determine the vector for which $$\theta = \left[0, \frac{\pi}{4}, \frac{\pi}{2}, \frac{3\pi}{4}, \pi, \frac{5\pi}{4}, \frac{3\pi}{2}, \frac{7\pi}{4}\right].$$

To increase computational efficiency, four neighboring electrodes 24 can be employed for which $$\theta = \left[0, \frac{\pi}{2}, \pi, \frac{3\pi}{2}\right]$$

where diagonal angles are excluded. Alternatively, the diagonal angles can be included instead for which $$\theta = \left[\frac{\pi}{4}, \frac{3\pi}{4}, \frac{5\pi}{4}, \frac{7\pi}{4}\right].$$

The processing system 32 can be configured to average the determined vector at each electrode location over a plurality of consecutive activation signals such that each vector is generated based on an average of a plurality of activation signals sensed over a selected time period.

In some embodiments, the processing system 32 generates a reliability index for each vector based on a contact between a mapping electrode 24 and the anatomical structure in contact with or directly adjacent to the corresponding electrode 24. Surrogate measures such as impedance/conductance or signals from a force/strain sensors placed adjacent to the electrodes could be used to determine a good contact versus bad contact between the electrode and tissue. In some cases, in spite of good tissue contact it may be hard to reliably pick up activations due to noisy signal. Reliability index could quantify the level of noise on the signal using measures such as signal-to-noise ratio. The reliability index can then be used to modify each vector to convey the reliability visually to a user. For example, the line weight or color can be modified to illustrate the reliability such as a thicker line can be identified as a more reliable vector than a thinner line. Since, in a typical activation map the amplitude of the voltage at an electrode location is visualized by a varying color spectrum, the reliability index of the activation signal at the corresponding electrode location is difficult to incorporate into typical activation maps in addition to the voltage information.

In some embodiments, the processing system 32 is configured to determine a signature pattern for each vector field map. Each vector field map can be compared to one or more of a plurality of vector field templates which are stored within a template bank. The vector bank can be a database or an array or a plurality of vector templates that are stored locally in memory in the processing system 32 or can be stored in a remote location and accessed via a network or internet connection. Each vector field template includes a vector field having a signature pattern and a location associated with the signature pattern. For example, the signature pattern may include patterns related to identifying a dominant rotor and/or divergent activation pattern associated with cardiac fibrillation. Each vector field template may include a unique signature pattern having an associated location wherein signature patterns include, for example, a curled pattern which can represent rotor activity including a rotor core and/or rotor path having a core location or a divergent pattern representing focal activity having a foci location.

Figure 5:
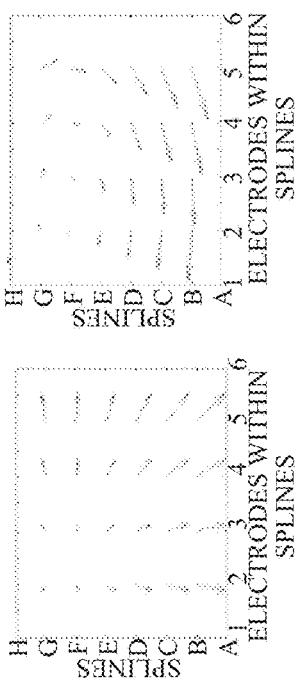
FIG. 5 illustrates a generated vector field map and a plurality of vector field templates employed by the processing system of FIG. 1.
Figure 5:
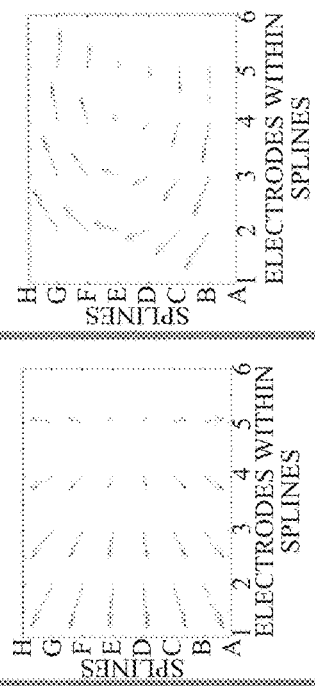
Figure 5:
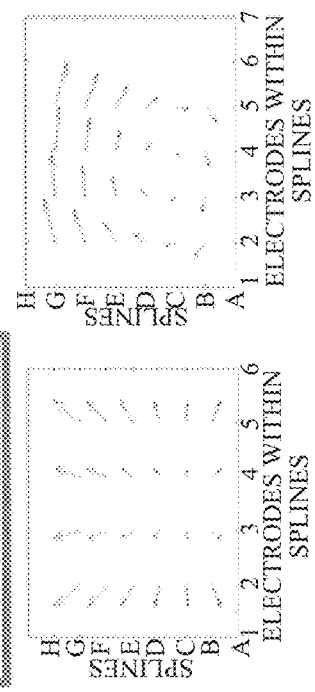

FIG. 5 illustrates an example of a generated vector field map 70 and six vector field templates 72 to which the processing system 32 can compare the vector field map 70. From vector field map 70, the vectors illustrate a divergent pattern with a foci location centered approximately at spline E and electrode 5. The processing system 32 can employ a distance based algorithm or a similarity based algorithm which will then compare each generated vector field to at least one of the vector field templates 72 in the template bank. The three templates 72 to the left illustrate divergent vector fields with foci locations centered in various positions, whereas the right three templates 72 illustrate curled vector fields with core locations at various positions. In some embodiments, the processing system 32 determines a similarity index P for each vector field template 72 based on a similarity algorithm applied to a generated vector field map. A vector field over N electrodes can be considered as a single "super-vector" in N×2 dimensional space. The index P is obtained by projecting the "super-vector" of the observed vector field onto a unit vector along the direction of the super-vector of the template vector field in the N×2 dimensional space. As illustrated in FIG. 5, the template 72 with P=1.82 has the highest similarity with generated vector field map 70. The template associated with P=1.82 has a divergent pattern with a foci located between electrodes 4 & 5 between splines D & E which is very similar to the generated vector field map 70. From the identified vector field template 72 and a foci location, the processing system 32 can output to the display device 40 the location of the corresponding template foci as a candidate for ablative therapy.

To compare a generated vector field map 70 to a vector field template 72, the processing system 32 projects the vectors of the vector field map onto the vector field template and then determines a similarity index based on a similarity algorithm and/or a distance algorithm. The vector field templates 72 can be normalized according to, for example, a Frobenius norm to yield vector field templates which are represented in terms of units templates.

In some embodiments, the processing system 32 determines a reliability index for each vector of a generated vector field map 70 and selects vectors that meet a preselected reliability threshold for comparison with the template bank. In other words, the processing system 32 determines a subset of vectors from a vector field map 70 and the template matching with the vector field templates is performed with reliable vectors. The determined reliability of a vector can be influenced by the conductance of mapping electrode 24 which sensed the activation signal corresponding to the vector. For example, if 36 mapping electrodes of a total of 64 mapping electrodes have a reliable detection of activation signals based on the determined reliability index, then the processing system 32 projects the 36 vectors associated with the 36 reliable mapping electrodes 24 onto each vector field template 72 for determining a similarity index. Since only a subset of vectors are used to determine the similarity index, the processing system 32 can determine the similarity index for each template 72 with increased efficiency due to a decrease in computation time and complexity because of the reduced number of projected vectors.

In some embodiments, the processing system 32 identifies a signature pattern and its corresponding location within a subset, sub-space, or region of each vector field map 70. Signature patterns and locations can be determined for a plurality of consecutive or subsequent vector field maps 72. The processing system 32 can identify signature patterns and locations in multiple distinct and/or overlapping subsets in parallel or sequentially. The signature patterns from the subsets can be employed to identify an overall global signature pattern for each entire vector field map 70. For example, the processing system 32 can generate a ranking of the signature patterns identified in all or preselected subsets corresponding to different regions of the anatomical structure. The global signature pattern can be identified according to the top ranked signature patterns identified in the distinct of overlapping subsets.

Once all vector fields are generated and a corresponding signature patterns and locations are identified, the processing system 32 can determine signature pattern locations which are candidates for therapy, such as ablative therapy, to reduce or eliminate a cardiac pathology such as fibrillation.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof

We claim:

1. A catheter system comprising:
   a plurality of mapping electrodes configured to detect activation signals of intrinsic cardiac activity, each of the plurality of mapping electrodes having an electrode location;
   a mapping processor associated with the plurality of mapping electrodes, the mapping processor configured to record the detected activation signals and associate one of the plurality of mapping electrodes with each recorded activation signal, the mapping processor further configured to generate a vector field map, comprising a plurality of vectors, which represents a direction of propagation of the activation signals at each electrode location, and identify a signature pattern and a target location in the vector field map according to at least one vector field template; and
   a display device configured to display the generated vector field map,
   wherein the mapping processor is further configured to determine a reliability index for each detected activation signal at an electrode location according to at least one of a contact between the corresponding electrode and an anatomical structure and a level of noise in the detected activation signal, and to modify the physical appearance of each of the plurality of vectors of the vector field map according to the corresponding reliability index to visually represent the reliability.

2. The catheter system according to claim 1, wherein to generate the vector field map the processing system is further configured to determine a vector of propagation at each electrode which represents a direction of propagation of the detected activation signal with respect to at least one adjacent electrode.

3. The catheter system according to claim 1, wherein to identify the signature pattern the processing system is further configured to access a template bank which includes a plurality of vector field templates, each vector field template having a unique signature pattern, compare the vector field map with each vector field template of the template bank, and identify the signature pattern most closely matching the generated vector field map according to a similarity index.

4. The catheter system according to claim 3, wherein each unique signature pattern of the template bank includes at least one of a divergent pattern representing focal activity having a foci location and a curled pattern representing rotor activity having a core location.

5. The catheter system according to claim 3, wherein to compare the vector field the processing system is further configured to determine a reliability index for each sensed activation signal at an electrode location according to at least one of a contact between the corresponding electrode and an anatomical structure and a level of noise in the detected activation signal, select one or more vectors of the vector field map which meet a preselected threshold based on the determine reliability index, and compare only the one or more selected vectors with the corresponding vectors within each vector field template of the template bank.

6. The catheter system according to claim 1, wherein the display device is further configured to display:
   the identified target location.

* * * * *